United States Patent
Miyazaki et al.

(10) Patent No.: US 10,183,158 B2
(45) Date of Patent: Jan. 22, 2019

(54) CONNECTING STRUCTURE FOR MEDICAL USE

(71) Applicant: KOYO SANGYO CO., LTD., Tokyo (JP)

(72) Inventors: Takayuki Miyazaki, Niigata (JP); Hiroki Watanabe, Niigata (JP); Mitsunari Sasagawa, Niigata (JP)

(73) Assignee: Koyo Sangyo Co., Ltd., Tokyo (JP)

( * ) Notice: Subject to any disclaimer, the term of this patent is extended or adjusted under 35 U.S.C. 154(b) by 92 days.

(21) Appl. No.: 15/102,557

(22) PCT Filed: Jan. 28, 2016

(86) PCT No.: PCT/JP2016/052474
§ 371 (c)(1),
(2) Date: Jun. 8, 2016

(87) PCT Pub. No.: WO2016/157974
PCT Pub. Date: Oct. 6, 2016

(65) Prior Publication Data
US 2017/0120032 A1    May 4, 2017

(30) Foreign Application Priority Data
Apr. 2, 2015 (JP) .................................. 2015-075582

(51) Int. Cl.
*A61M 39/00* (2006.01)
*A61M 39/10* (2006.01)
(Continued)

(52) U.S. Cl.
CPC ........ *A61M 39/1055* (2013.01); *A61M 39/10* (2013.01); *A61M 5/178* (2013.01);
(Continued)

(58) Field of Classification Search
CPC .... A61M 2039/1038; A61M 2039/229; A61M 39/1055; A61M 5/178
See application file for complete search history.

(56) References Cited

U.S. PATENT DOCUMENTS 5,520,666 A * 5/1996 Choudhury ......... A61M 39/045
604/537
6,152,913 A * 11/2000 Feith .................... A61M 39/10
604/533

(Continued)

FOREIGN PATENT DOCUMENTS

| JP | S62-116740 U | 7/1987 |
| JP | 2001-187990 A | 7/2001 |

(Continued)

OTHER PUBLICATIONS

Extended European Search Report for corresponding European application No. 16730235.5 dated Jan. 4, 2018.
(Continued)

*Primary Examiner* — Quynh-Nhu H Vu
(74) *Attorney, Agent, or Firm* — Thomas B. Ryan, Patent Agent; Harter Secrest & Emery LLP

(57) ABSTRACT

A connecting structure for medical use includes a first connecting portion 1 and a second connecting portion 2. The first connecting portion 1 includes a threadedly engageable portion 22*a*, a support portion 22*b* and a sealing portion 14. The second connecting portion 2 includes a threadedly engageable portion 2*c* and a sealing portion 2*b*. The threadedly engageable portions are threadedly engageable with each other. The sealing portions are joinable to each other by advancement of a threaded engagement between the threadedly engageable portions. An operating cylinder 30 is mounted on an outer periphery of the support portion 22*b*. A torque limiting mechanism 40 is disposed between the operating cylinder 30 and the support portion 22*b*. The
(Continued)

sealing portions 14, 2b can be joined by turning the operating cylinder 30 in a threaded engagement advancing direction. When a rotary torque applied to the operating cylinder 30 reaches a predetermined torque as a result of a resistance generated by the joining of the sealing portions, the operating cylinder 30 is turned free from the support portion 22b. By this arrangement, appropriate sealing properties can be secured and the sealing portions can be prevented from breakages.

4 Claims, 18 Drawing Sheets

(51) Int. Cl.
*A61M 5/178* (2006.01)
*A61M 39/22* (2006.01)

(52) U.S. Cl.
CPC ............ *A61M 2039/1038* (2013.01); *A61M 2039/1044* (2013.01); *A61M 2039/229* (2013.01)

(56) References Cited

U.S. PATENT DOCUMENTS

| | | | | |
|---|---|---|---|---|
| 8,465,322 B2* | 6/2013 | Purdy | ............... | H01R 9/0524 |
| | | | | 439/584 |
| 8,777,931 B2* | 7/2014 | Davis | ............... | A61M 39/10 |
| | | | | 604/533 |
| 2007/0129705 A1* | 6/2007 | Trombley, III | ........ | A61M 39/10 |
| | | | | 604/523 |
| 2008/0004600 A1* | 1/2008 | Kitani | ................ | A61M 39/10 |
| | | | | 604/533 |
| 2008/0172039 A1 | 7/2008 | Raines | | |
| 2010/0036329 A1* | 2/2010 | Razack | ............. | A61M 39/0613 |
| | | | | 604/256 |
| 2012/0046649 A1* | 2/2012 | Bierman | ............... | A61M 39/10 |
| | | | | 604/535 |
| 2015/0167874 A1* | 6/2015 | Buerli | ................ | F16L 37/138 |
| | | | | 285/242 |

FOREIGN PATENT DOCUMENTS

| | | |
|---|---|---|
| JP | 3108468 U | 4/2005 |
| JP | 2007-309485 A | 11/2007 |
| JP | 2013-521093 A | 6/2013 |
| JP | 2013-208206 A | 10/2013 |
| WO | 02 096500 A1 | 12/2002 |
| WO | 2011/110888 A1 | 9/2011 |

OTHER PUBLICATIONS

International Search Report (English Version) for PCT/JP2016/052474 dated Apr. 19, 2016.
PCT Written Opinion from corresponding PCT/JP2016/052474 dated Aug. 29, 2016.
Japanese Office Action for corresponding Japanese application No. 2016-536789 dated Jun. 5, 2018.

* cited by examiner

CONNECTING STRUCTURE FOR MEDICAL USE

FIELD OF THE INVENTION

The present invention relates to a connecting structure for medical use.

BACKGROUND OF THE INVENTION

As disclosed in unexamined Japanese Utility Model Publication No. S62-116740, a connecting structure for medical use that includes a male connector and a female connector for connecting medical components such as tubes are well known. The male connector includes a male luer portion having a tapered outer periphery. The female connector includes a female luer portion having a tapered inner periphery. The male connector and the female connector are threadedly engageable with each other. The male luer portion and the female luer portion can be joined together with a pressing force working therebetween by advancement of the threaded engagement between the male connector and the female connector. By this arrangement, desired sealing properties can be obtained.

When the connectors are not threadedly engaged tightly enough in the connecting structure mentioned above, sufficient sealing properties may not be obtained. Without sufficient sealing properties, the connectors may be disconnected when subjected to impact.

When the connectors are threadedly engaged too tightly, the male luer portion and the female luer portion may bite strongly into each other. In such a state, the threaded engagement between the connectors may not be able to be loosened. Accordingly, the connectors may not be able to be disconnected from each other nor connected to another connector. Excessive tightening torque may cause breakages such as cracking to the male luer portion and the female luer portion.

Granted Japanese Utility Model Publication No. 3108468 discloses a stopper provided in one of the male connector and the female connector. Depth of threaded engagement is controlled by the stopper in order to prevent excessive tightening.

However, according to the features disclosed in Japanese Utility Model Publication No. 3108468, manufacturing errors may cause an error in a relationship between the controlled depth of threaded engagement and a tightening torque for securing appropriate sealing properties. Sometimes, the error in the relationship may be so significant that the appropriate sealing properties and the prevention of excessive tightening cannot be realized at the same time.

SUMMARY OF THE INVENTION

To solve the problems mentioned above, the present invention provides a connecting structure for medical use including: a first connecting portion; and a second connecting portion wherein: the first connecting portion includes a first threadedly engageable portion and the second connecting portion includes a second threadedly engageable portion, the first threadedly engageable portion and the second threadedly engageable portion being threadedly engageable with each other; the first connecting portion includes a first sealing portion and the second connecting portion includes a second sealing portion, the first sealing portion and the second sealing portion being joinable to each other by advancement of a threaded engagement between the first threadedly engageable portion and the second threadedly engageable portion; one of the first sealing portion and the second sealing portion is a male luer portion having a tapered outer periphery and the other of the first sealing portion and the second sealing portion is a female luer portion having a tapered inner periphery; and the male luer portion and the female luer portion can be sealed together by joining the outer periphery of the male luer portion and the inner periphery of the female luer portion, wherein the first connecting portion includes a support portion that is integral with the first threadedly engageable portion; an operating cylinder is mounted on an outer periphery of the support portion; a torque limiting mechanism is disposed between the support portion of the first connecting portion and the operating cylinder; and the torque limiting mechanism is constructed and arranged such that: when the operating cylinder is turned in a threaded engagement loosening direction with respect to the second connecting portion, the support portion of the first connecting portion is turned together with the operating cylinder; in a process in which the operating cylinder is turned in a threaded engagement advancing direction with respect to the second connecting portion, the support portion of the first connecting portion is turned together with the operating cylinder until a rotary torque applied to the operating cylinder reaches a predetermined torque; and in the process in which the operating cylinder is turned in the threaded engagement advancing direction with respect to the second connecting portion, the operating cylinder is turned free from the support portion of the first connecting portion when the rotary torque applied to the operating cylinder reaches the predetermined torque as a result of a resistance generated by the joining of the first sealing portion and the second sealing portion.

According to the features mentioned above, adequate sealing properties between the first sealing portion and the second sealing portion can be surely provided by the predetermined torque and an excessive tightening can be avoided. Therefore, the first sealing portion and the second sealing portion can be prevented from breakages and from biting into each other.

Preferably, the torque limiting mechanism includes one or a plurality of first engageable portions formed in the support portion of the first connecting portion and one or a plurality of second engageable portions formed in the operating cylinder; when the operating cylinder is turned in the threaded engagement loosening direction with respect to the second connecting portion, one side of the second engageable portion is caught by one side of the first engageable portion opposed to the one side of the second engageable portion in a circumferential direction, thereby the support portion of the first connecting portion being turned together with the operating cylinder; in the process in which the operating cylinder is turned in the threaded engagement advancing direction with respect to the second connecting portion, the other side of the second engageable portion is caught by the other side of the first engageable portion, thereby the support portion of the first connecting portion being turned together with the operating cylinder until the rotary torque applied to the operating cylinder reaches the predetermined torque; and in the process in which the operating cylinder is turned in the threaded engagement advancing direction with respect to the second connecting portion, the second engageable portion is moved beyond the first engageable portion when the rotary torque applied to the operating cylinder reaches the predetermined torque as a result of the resistance generated by the joining of the first sealing portion and the second sealing portion, thereby the operating cylinder being turned free.

According to the features given above, the torque limiting mechanism can be of a relatively simple structure.

Preferably, the one side of the second engageable portion includes a steep catch surface and the one side of the first engageable portion includes a steep catch surface; and at least one of the other side of the second engageable portion and the other side of the first engageable portion includes an inclined surface.

According to the features given above, when the operating cylinder is turned in the threaded engagement loosening direction, the catch surface of the first engageable portion and the catch surface of the second engageable portion are abutted against each other, thereby the first connecting portion and the second connecting portion can be surely disconnected from each other. When the operating cylinder is turned in the threaded engagement advancing direction, torque can be controlled by an action of the inclined surface of at least one of the first engageable portion and the second engageable portion.

Preferably, the operating cylinder is mounted on the support portion of the first connecting portion such that the operating cylinder is not movable in an axial direction; the support portion includes an annular first engaging area in the outer periphery thereof and the operating cylinder includes an annular second engaging area in an inner periphery thereof, the first engaging area and the second engaging area opposed to each other in a radial direction; the plurality of first engageable portions are formed in the first engaging area evenly spaced apart in a circumferential direction; the plurality of second engageable portions are formed in the second engaging area evenly spaced apart in a circumferential direction; and when the rotary torque applied to the operating cylinder reaches the predetermined torque, the second engageable portions are moved beyond the first engageable portions accompanied by an elastic deformation of the operating cylinder.

According to the features given above, the torque can be controlled by utilizing elasticity of the operating cylinder, which allows for simplification of the features. When the operating cylinder turns idly, a clicking sound is generated when the second engageable portion is elastically returned after being moved beyond the first engageable portion. Thereby, a connection worker can learn that the predetermined torque has been reached.

Preferably, a plurality of elastically deformable portions are formed in the operating cylinder evenly spaced apart in a circumferential direction; the elastically deformable portions are elastically deformable in a radial direction independently from each other; and the elastically deformable portions respectively have the second engageable portions formed in inner surfaces thereof.

According to the features given above, the torque can be controlled by utilizing elasticity of the plurality of elastically deformable portions.

Preferably, the operating cylinder has a plurality of slits extending in the axial direction thereof formed in one end portion thereof in the axial direction, the plurality of slits evenly spaced apart in the circumferential direction; and areas between the slits are provided as the elastically deformable portions.

According to the features given above, the elastically deformable portion can be of a simple configuration.

Alternatively, the operating cylinder may have a plurality of slits having U-shaped configurations formed evenly spaced apart in the circumferential direction; and areas surrounded by the slits are provided as the elastically deformable portions.

In one aspect of the present invention, engagement recesses as the first engageable portions are formed in the first engaging area of the support portion; engagement protrusions as the second engageable portions are formed in the second engaging area of the operating cylinder; and in a condition where the rotary torque is not applied to the operating cylinder, the engagement protrusions are received in the engagement recesses.

In another aspect of the present invention, engagement protrusions as the first engageable portions are formed in the first engaging area of the support portion; engagement recesses as the second engageable portions are formed in the second engaging area of the operating cylinder; and in a condition where the rotary torque is not applied to the operating cylinder, the engagement protrusions are received in the engagement recesses.

The first connecting portion is disposed in a first medical component that includes a passage; the second connecting portion is disposed in a second medical component that includes a passage; and the passage of the first medical component and the passage of the second medical component are brought to communicate with each other by connection of the first connecting portion and the second connecting portion.

Examples of a medical component may include a tube, a stopper cock and a syringe.

In one embodiment of the present invention applied in a syringe, the first connecting portion includes a female luer member and a cylindrically-shaped attachment removably attachable to the female luer member. The female luer member includes the female luer portion as the first sealing portion. The attachment includes a cylindrical portion. An outer periphery of the cylindrical portion is provided as the support portion. An inner periphery of the cylindrical portion has a female screw portion as the first threadedly engageable portion formed therein. A liquid outlet portion of the syringe is provided as the second connecting portion. The liquid outlet portion includes the male luer portion as the second sealing portion and a male screw portion as the second threadedly engageable portion in a distal end portion thereof.

One of the first connecting portion and the second connecting portion is disposed in a medical component that includes a passage; and the other of the first connecting portion and the second connecting portion is provided as a closing member that can close the passage.

According to the features given above, tightening torque can be controlled in a connecting work of the closing member that can close the passage of the medical component.

According to the present invention, appropriate sealing properties can be secured and excessive tightening can be prevented in a connecting structure for medical use.

Details of the present invention will be described hereinafter with reference to the drawings.

DETAILED DESCRIPTION

Figure 1A:
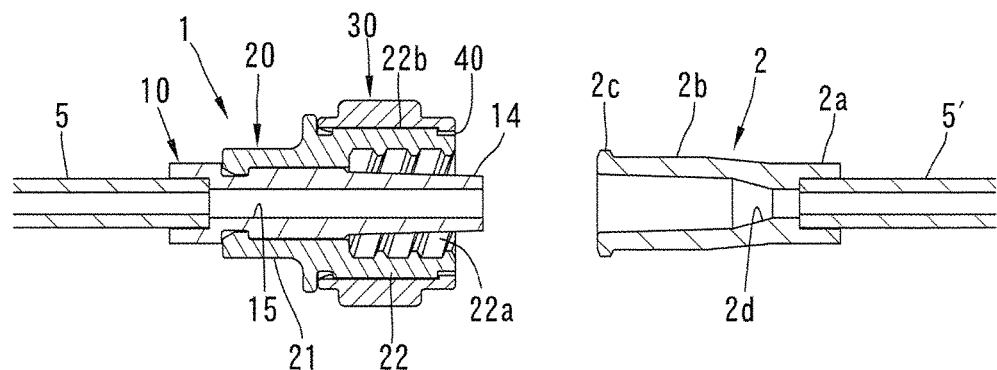
FIG. 1A is a cross-sectional view of a connecting structure for medical use according to a first embodiment of the present invention applied to connect tubes, showing a male connector and a female connector separate from each other.
Figure 1B:
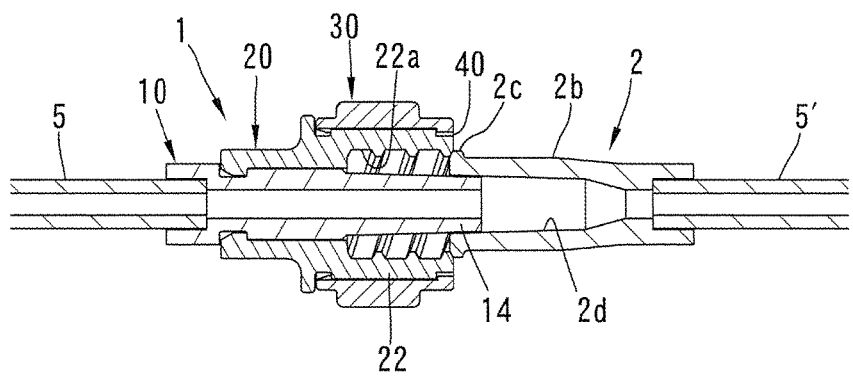
FIG. 1B is a cross-sectional view of the connecting structure for medical use at a start of a connection work.
Figure 1C:
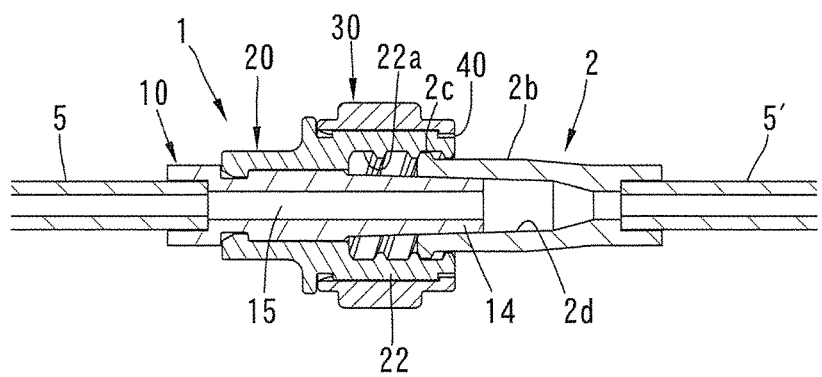
FIG. 1C is a cross-sectional view of the connecting structure for medical use on completion of the connection work.

FIGS. 1 to 6 show a connecting structure for medical use according to a first embodiment of the present invention, which is applied to connect tubes 5, 5' (first and second medical components) in which liquid such as medical solution and blood is to be flown. As shown in FIG. 1, the connecting structure includes a male connector 1 (first connecting portion) and a female connector 2 (second connecting portion).

The female connector 2 having a simpler structure will be described first. The female connector 2 is provided as a female luer member having a thin and long cylindrical configuration. The female connector 2 includes a coupling portion 2a and a female luer portion 2b (second sealing portion), which are arranged in a direction from a basal end of the female connector 2 to a distal end of the female connector 2. A distal end of the tube 5' is inserted into and fixed in the coupling portion 2a. A pair of protrusions 2c (second threadedly engageable portions) are formed in an outer periphery of a distal end portion of the female luer portion 2b 180 degrees apart from each other in a circumferential direction.

An inner periphery of the female luer portion 2b has a gently tapered configuration whose diameter is gradually increased towards a distal end of the female luer portion 2b. The female connector 2 includes a passage 2d extending therethrough along a central axis thereof. The passage 2d communicates with a passage of the tube 5'.

The male connector 1 includes a male luer member 10 and a threadedly engageable member 20 mounted on an outer periphery of the male luer member 10 such that the threadedly engageable member 20 is rotatable but immovable in an axial direction.

Figure 4:
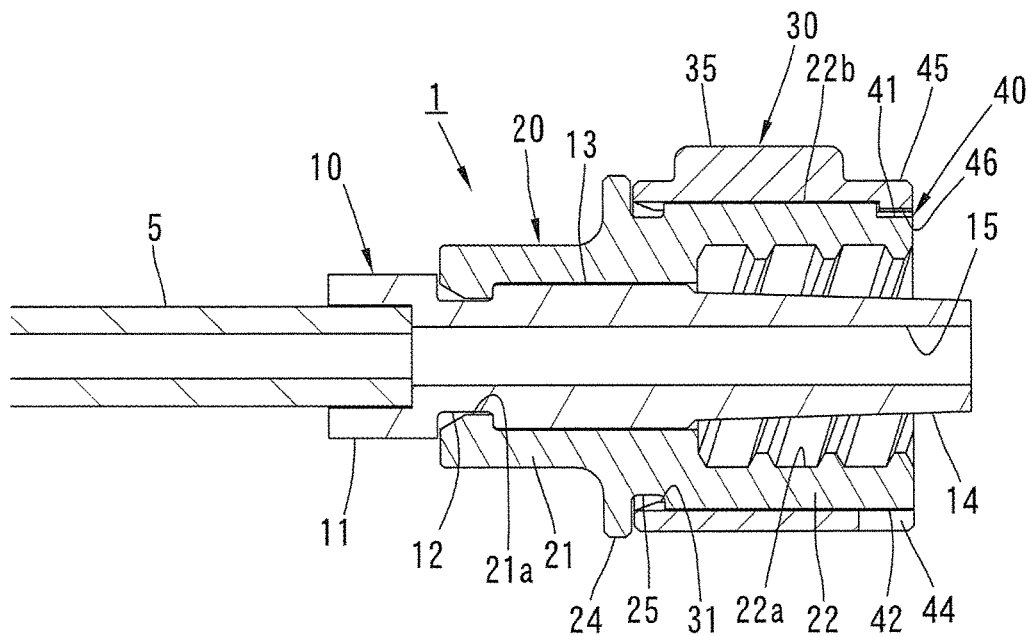
FIG. 4 is an enlarged cross-sectional view of the male connector and the operating cylinder.
Figure 5:
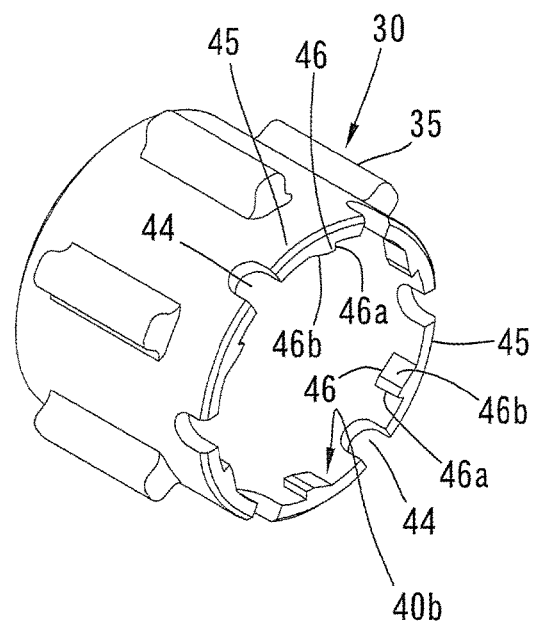
FIG. 5 is a perspective view of the operating cylinder.

As shown in FIG. 4, the male luer member 10 has a thin and long cylindrical configuration. The male luer member 10 includes a coupling portion 11, a receiving portion 13 and a male luer portion 14 (first sealing portion), which are arranged in a direction from a basal end of the male luer member 10 to a distal end of the male luer member 10. A distal end of the tube 5 is inserted into and fixed in the coupling portion 11. An outer periphery of the receiving portion 13 is provided as a circular cylindrical surface. An outer periphery of the male luer portion 14 has a tapered configuration whose diameter is gradually reduced towards a distal end of the male luer portion 14. A taper angle of the outer periphery of the male luer portion 14 and a taper angle of the inner periphery of the female luer portion 2b are substantially the same. An engagement groove 12 having an annular configuration is formed in the outer periphery of the male luer member 10 at a boundary of the coupling portion 11 and the receiving portion 13.

The male luer member 10 includes a passage 15 extending therethrough along a central axis thereof. The passage 15 communicates with a passage of the tube 5.

The threadedly engageable member 20 has a cylindrical configuration and includes a circular cylindrical portion 21 on a basal side thereof and a circular cylindrical portion 22 on a distal side thereof. The circular cylindrical portion 21 has a small diameter and the circular cylindrical portion 22 has a large diameter. An annular engagement protrusion 21a protruding inwardly in a radial direction is formed in a basal end of the circular cylindrical portion 21.

When the threadedly engageable member 20 is pushed in the axial direction from the distal end of the male luer member 10, the engagement protrusion 21a is fitted in the engagement groove 12 of the male luer member 10 and the circular cylindrical portion 21 of the threadedly engageable member 20 is disposed outside of the receiving portion 13 of the male luer member 10 in a radial direction. Thereby, the threadedly engageable member 20 is connected to the male luer member 10 such that the threadedly engageable member 20 is rotatable but relatively immovable in the axial direction with respect to the male luer member 10. In this connected state, an annular insertion space is formed between the circular cylindrical portion 22 of the threadedly engageable member 20 and the male luer portion 14 of the male luer member 10.

A female screw portion 22a (first threadedly engageable portion) is formed in an inner periphery of the circular cylindrical portion 22.

The connecting structure for medical use of the present invention further includes an operating cylinder 30. As shown in FIG. 4, an outer periphery of the circular cylindrical portion 22 of the threadedly engageable member 20 of the male connector 1 is provided as a support portion 22b. The operating cylinder 30 is disposed outside of the support portion 22b in a radial direction and is rotatably supported by the support portion 22b.

The operating cylinder 30 is immovable with respect to the threadedly engageable member 20 in an axial direction. Specifically, an annular catch groove 25 is formed in a basal end portion of the support portion 22b of the threadedly engageable member 20. An annular catch wall 24 is formed adjacent to the catch groove 25. A plurality of engagement protrusions 31 are formed in an inner periphery of a basal end of the operating cylinder 30 spaced from each other in the circumferential direction. When the operating cylinder 30 is pushed in the axial direction from the distal end of the threadedly engageable member 20, the engagement protrusions 31 are fitted in the catch groove 25 of the threadedly engageable member 20. The engagement protrusions 31 are caught by a side surface of the catch groove 25 and the catch wall 24. Thereby, the operating cylinder 30 is connected to the threadedly engageable member 20 such that the operating cylinder 30 is relatively immovable in the axial direction with respect to the threadedly engageable member 20.

Elongated raised portions 35 for placing fingers thereon are formed in an outer periphery of the operating cylinder 30 evenly spaced apart in the circumferential direction.

A torque limiting mechanism 40 is disposed between a distal end portion of the threadedly engageable member 20 and a distal end portion of the operating cylinder 30. Detailed description of the torque limiting mechanism 40 is provided below.

Figure 3:
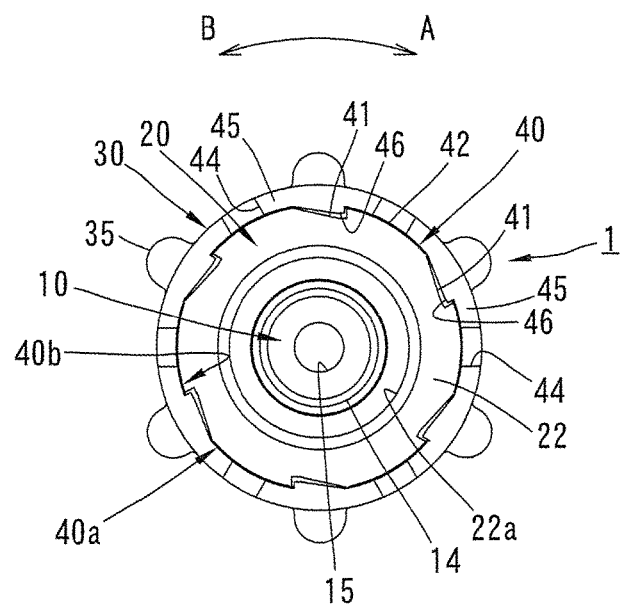
FIG. 3 is a front view of the male connector and the operating cylinder, viewed from the direction of arrow X of FIG. 2.

As shown in FIGS. 3 and 4, an outer periphery of a distal end portion of the support portion 22b of the threadedly engageable member 20 is provided as an annular first engaging area 40a. A plurality of engagement recesses 41 (first engageable portions) are formed in the first engaging area 40a evenly spaced apart in a circumferential direction. Areas between adjacent engagement recesses 41 are circular arc surfaces 42.

Figure 2:
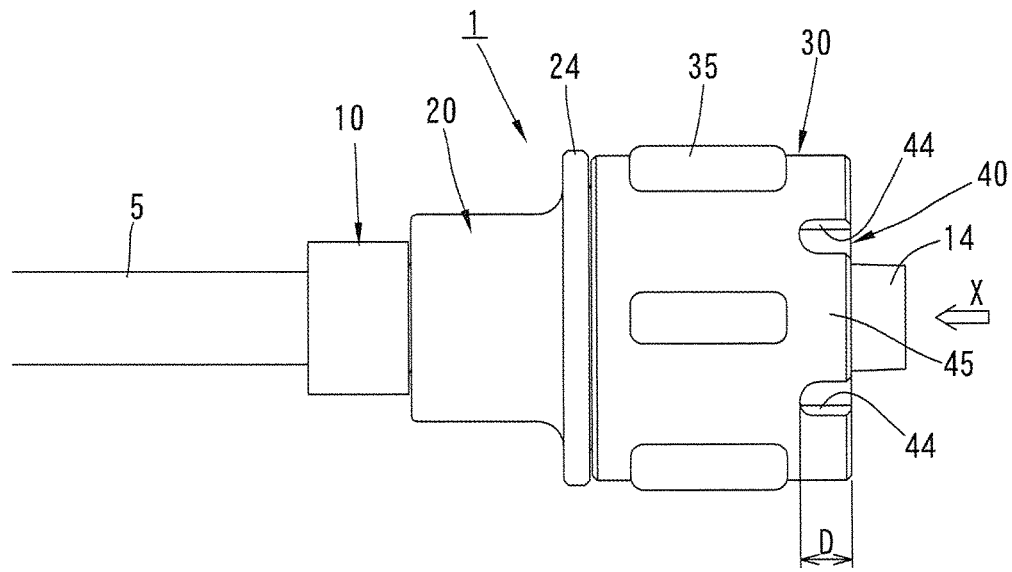
FIG. 2 is a side view of the male connector and an operating cylinder mounted on the male connector.

An inner periphery of the distal end portion of the operating cylinder 30 is provided as an annular second engaging area 40b. Specifically, slits 44 are formed in the distal end portion of the operating cylinder 30 evenly spaced apart in a circumferential direction. The slits 44 extend in an axial direction from a distal end surface of the operating cylinder 30 through a predetermined length D (FIG. 2). Areas between adjacent slits 44 are elastically deformable portions 45. The elastically deformable portions 45 are elastically deformable in a radial direction of the operating cylinder 30. An engagement protrusion 46 (second engageable portion) is formed in an inner surface of a distal end portion of each of the elastically deformable portions 45. A dimension of the engagement protrusion 46 in an axial direction is smaller than the length D of the slit 44, which allows the elastically deformable portion 45 to be easily elastically deformed.

As shown in FIG. 3, the first engaging area 40a and the second engaging area 40b are opposed to each other in a radial direction. In a condition where a rotational torque is not applied to the operating cylinder 30, the engagement protrusions 46 are received in the engagement recesses 41.

Figure 6A:
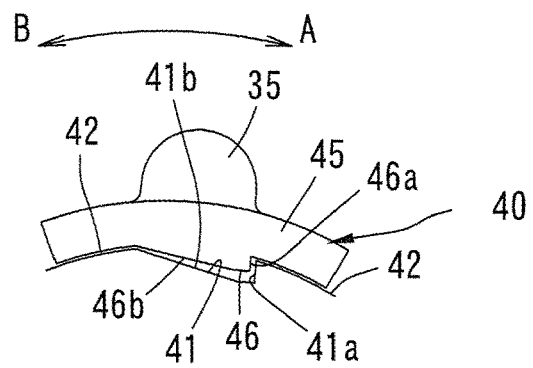
FIG. 6A is an enlarged view of a principal part of a torque limiting mechanism between the male connector and the operating cylinder before the operating cylinder is turned.

As shown in FIG. 6A, the engagement protrusion 46 of the operating cylinder 30 includes a steep catch surface 46a on a threaded engagement loosening direction A side and a gently inclined surface 46b on a threaded engagement advancing direction B side.

The engagement recess 41 of the threadedly engageable member 20 includes a steep catch surface 41a on one side in a circumferential direction thereof and a gently inclined surface 41b on the other side in the circumferential direction thereof. The steep catch surface 41a is opposed to the catch surface 46a of the engagement protrusion 46 in the circumferential direction. Specifically, an angle of the catch surface 41a and an angle of the catch surface 46a with respect to the circumferential direction are great, i.e. about 90 degrees. An angle of the inclined surface 41b and an angle of the inclined surface 46b with respect to the circumferential direction are small, i.e. about 30 to 40 degrees.

The tubes 5, 5' are connected using the connecting structure having the features mentioned above in the following manner. The male connector 1 and the female connector 2 are arranged coaxially as shown in FIG. 1A and brought closer to each other. Then, as shown in FIG. 1B, the male luer portion 14 of the male connector 1 is inserted in a distal end portion of the female luer portion 2b of the female connector 2.

The insertion proceeds without resistance until the protrusions 2c of the female connector 2 are abutted against an opening end of the female screw portion 22a of the male connector 1.

Figure 6B:
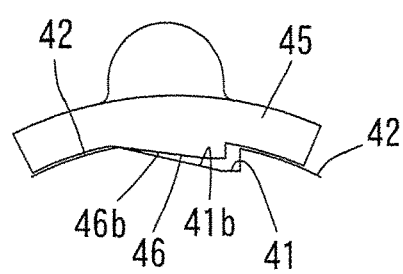
FIG. 6B is an enlarged view of a principal part of the torque limiting mechanism when the operating cylinder is turned to advance threaded engagement between the male connector and the female connector.

Next, the operating cylinder 30 is turned in the threaded engagement advancing direction B shown in FIGS. 3 and 6A. This causes the inclined surfaces 46b of the engagement protrusions 46 of the operating cylinder 30 to be abutted against the inclined surfaces 41b of the engagement recesses 41 of the threadedly engageable member 20 as shown in FIG. 6B. This causes the threadedly engageable member 20 to be rotated with the operating cylinder 30. Thereby, the threaded engagement between the protrusions 2c of the female connector 2 and the female screw portion 22a of the threadedly engageable member 20 is advanced. At an initial stage of the threaded engagement, little resistance is met. Therefore, the operating cylinder 30 and the threadedly engageable member 20 are turned together with a small rotary torque, advancing the threaded engagement and causing little deformation of the elastically deformable portions 45 outwardly in the radial direction. Accompanying the advancement of the threaded engagement, the female luer portion 2b enters an insertion space between the male luer portion 14 and the female screw portion 22a.

Figure 6C:
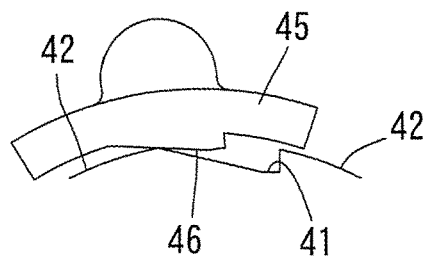
FIG. 6C is an enlarged view of a principal part of the torque limiting mechanism when the threaded engagement is advanced further and a rotary torque of the operating cylinder has increased.

As the threaded engagement is advanced, a depth of insertion of the male luer portion 14 into the female luer portion 2b is increased. This brings the male luer portion 14 and the female luer portion 2b to be joined together with frictional resistance therebetween increased. As a result, a torque required for turning the operating cylinder 30 is increased. Accordingly, as shown in FIG. 6C, the engagement protrusions 46 of the operating cylinder 30 are relatively displaced with respect to the engagement recesses 41 in a circumferential direction. As a result of actions of the inclined surfaces 41b, 46b, amounts of elastic deformation of the elastically deformable portions 45 in the radius direction are increased.

Figure 6D:
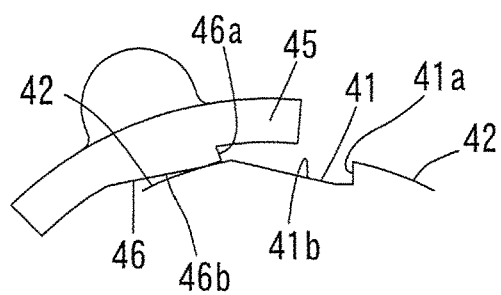
FIG. 6D is an enlarged view of a principal part of the torque limiting mechanism when the rotary torque of the operating cylinder has reached a predetermined torque and the operating cylinder turns idly.

As the threaded engagement is advanced further, the rotary torque of the operating cylinder 30 reaches a predetermined torque and the male luer portion 14 and the female luer portion 2b are joined together with a sufficient pressing force for exercising appropriate sealing properties working therebetween. At this time, as shown in FIG. 6D, the engagement protrusions 46, having been moved out of the engagement recesses 41, slide on the circular arc surfaces 42. This causes the operating cylinder 30 to be tuned idly. Therefore, the rotary torque of the operating cylinder 30 is not transmitted to the threadedly engageable member 20, thereby the rotation of the threadedly engageable member 20 may be stopped.

As mentioned above, the torque is controlled such that an upper limit of the rotary torque transmitted from the operating cylinder 30 to the threadedly engageable member 20 is the predetermined torque. Therefore, the pressing force working between the male luer portion 14 and the female luer portion 2b can be controlled so as not to be excessive but sufficient to exercise the sufficient sealing properties. As a result, liquid can be flown in the tube 5, passages 15, 2d and the tube 5' without leakage. Moreover, breakages of the male luer portion 14 and the female luer portion 2b caused by the application of excessive torque can be avoided.

If the tubes 5, 5' need to be disconnected after they are connected in the manner described above, the operating cylinder 30 may be turned in the threaded engagement loosening direction A. This causes the catch surfaces 46a of the engagement protrusions 46 of the operating cylinder 30 to be abutted against the catch surfaces 41a of the engagement recesses 41 of the threadedly engageable member 20, thereby causing the threadedly engageable member 20 to be turned with the operating cylinder 30 in the threaded engagement loosening direction. As a result, the male luer portion 14 and the female luer portion 2b are disjoined from each other and consequently, the connectors 1, 2 are separated from each other.

When the threaded engagement is loosened in the manner described above, the steep catch surfaces 41a, 46a are abutted against each other. Therefore, the operating cylinder 30 can provide the threadedly engageable member 20 with a torque that is greater than the upper limit torque transmitted as the threaded engagement is advanced. Therefore, the threaded engagement can be surely loosened.

Since the male lure portion 14 and the female luer portion 2b are joined together with the appropriate pressing force working therebetween as mentioned above, the male lure portion 14 and the female luer portion 2b can be prevented from biting into each other. Therefore, excessive rotary torque is not required for loosening the threaded engagement and no excessive torsional stress works on the male lure portion 14 and the female luer portion 2b. Therefore, breakage of the luer portions 14, 2b can be avoided and the connectors 1, 2 can be reconnected to other connectors.

Figure 7A:
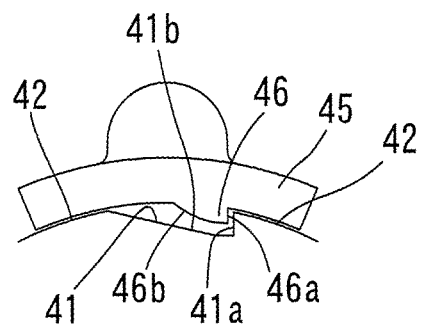
FIG. 7A is a view, showing a modification example of an engagement protrusion as a second engageable portion of the torque limiting mechanism.
Figure 7B:
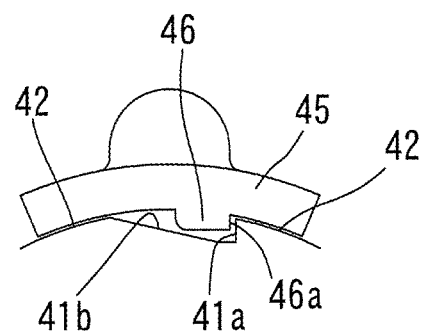
FIG. 7B is a view, showing another modification example of the engagement protrusion.
Figure 7C:
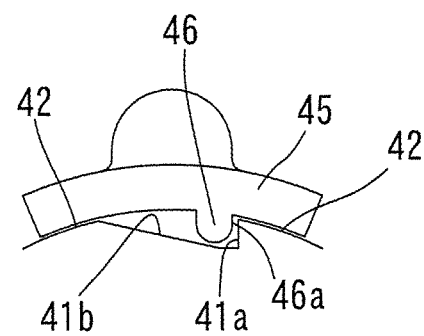
FIG. 7C is a view, showing another modification example of the engagement protrusion.

The engagement protrusions 46 of the operating cylinder 30 can have a variety of configurations. For example, as shown in FIG. 7A, a dimension of the engagement protrusion 46 in a circumferential direction can be about a half of a dimension of the engagement recess 41 in a circumferential direction. In this case, torque is transmitted by abutment of the inclined surface 46b of the engagement protrusion 46 against a generally central portion of the inclined surface 41b of the engagement recess 41. Alternatively, as shown in FIGS. 7B and 7C, the engagement protrusion 46 may have no inclined surface.

When the engagement protrusion 46 has the inclined surface 46b, the engagement recess 41 may not have an inclined surface.

Other embodiments of the present invention will be described hereinafter with reference to the accompanying drawings. Same or similar reference numerals are used to designate parts that correspond to those in foregoing embodiments and description thereof will be omitted.

Figure 8:
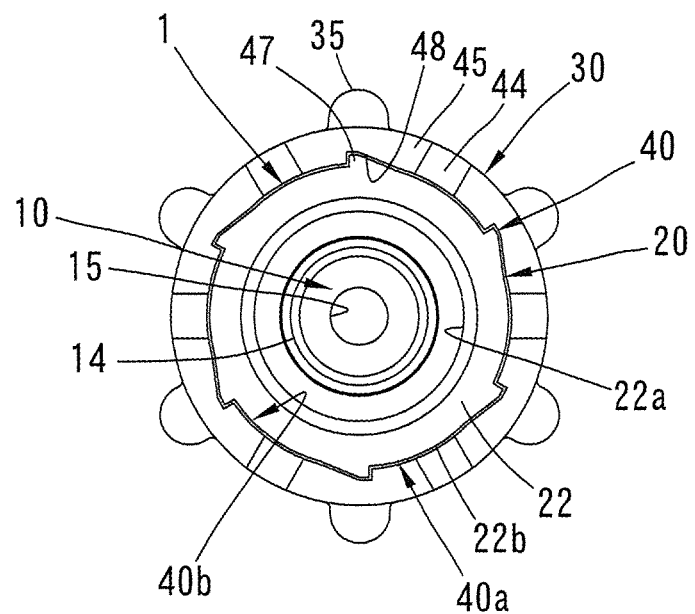
FIG. 8 is a front view of a male connector and an operating cylinder of a connecting structure for medical use according to a second embodiment of the present invention.
Figure 9:
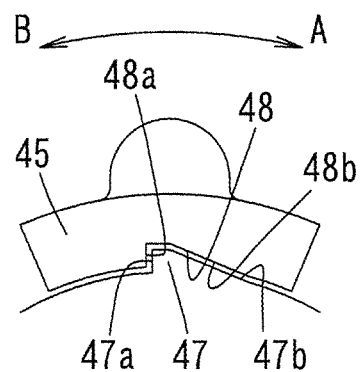
FIG. 9 is an enlarged view of a principal part of a torque limiting mechanism according to the second embodiment.

In a second embodiment shown in FIGS. 8 and 9, engagement protrusions 47 (first engageable portions) are formed in a first engaging area 40a in an outer periphery of a distal end portion of a support portion 22b of a male connector 1. The engagement protrusions 47 are formed evenly spaced apart in a circumferential direction and protrude from a circular cylindrical surface of the first engaging area 40a. Engagement recesses 48 (second engageable portions) are formed in a second engaging area 40b in an inner periphery of a distal end portion of an operating cylinder 30. The engagement recesses 48 are formed evenly spaced apart in a circumferential direction. Specifically, the engagement recess 48 is formed in each of inner surfaces of elastically deformable portions 45.

As with the first embodiment, the engagement protrusion 47 includes a catch surface 47a and an inclined surface 47b and the engagement recess 48 includes a catch surface 48a and an inclined surface 48b. The catch surface 47a and the inclined surface 47b are arranged in reverse positions compared with the catch surface 41a and the inclined surface 41b of the first embodiment. Similarly, the catch surface 48a and the inclined surface 48b are arranged in reverse positions compared with the catch surface 46a and the inclined surface 46b of the first embodiment.

In the second embodiment described above, when the operating cylinder 30 is turned in a threaded engagement advancing direction B (see FIG. 9), the inclined surfaces 48b of the engagement recesses 48 of the operating cylinder 30 are abutted against the inclined surfaces 47b of the engagement protrusions 47 of a threadedly engageable member 20. This causes the threadedly engageable member 20 to be turned with the operating cylinder 30. As the threaded engagement is advanced, a torque required for turning the operating cylinder 30 is increased. When the torque reaches a predetermined torque, the engagement recesses 48 are moved out of the engagement protrusions 47 and the engagement protrusions 47 slide on circular arc surfaces of the elastically deformable portions 45.

When the operating cylinder 30 is turned in a threaded engagement loosening direction A, the catch surfaces 48a of the engagement recesses 48 of the operating cylinder 30 are abutted against the catch surfaces 47a of the engagement protrusions 47 of the threadedly engageable member 20. This causes the threadedly engageable member 20 to be turned with the operating cylinder 30 in the threaded engagement loosening direction.

Figure 10A:
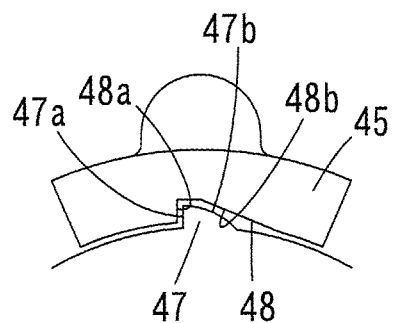
FIG. 10A is a view showing a modification example of an engagement protrusion as a first engageable portion of the torque limiting mechanism according to the second embodiment.
Figure 10B:
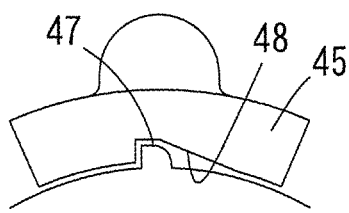
FIG. 10B is a view showing another modification example of the engagement protrusion.
Figure 10C:
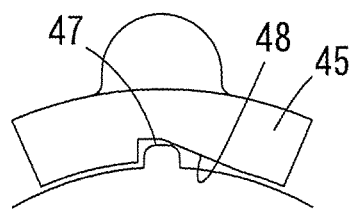
FIG. 10C is a view showing another modification example of the engagement protrusion.

As shown in FIGS. 10A to 10C, the engagement protrusions 47 can have a variety of configurations in the second embodiment. Since the configuration of the engagement protrusions 47 shown in FIGS. 10A to 10C are respectively similar to the configuration of the engagement protrusions 46 shown in FIGS. 7A to 7C, description of the configuration of the engagement protrusions 47 is omitted.

When the engagement protrusion 47 has the inclined surface 47b, the engagement recess 48 may not have an inclined surface.

Figure 11:
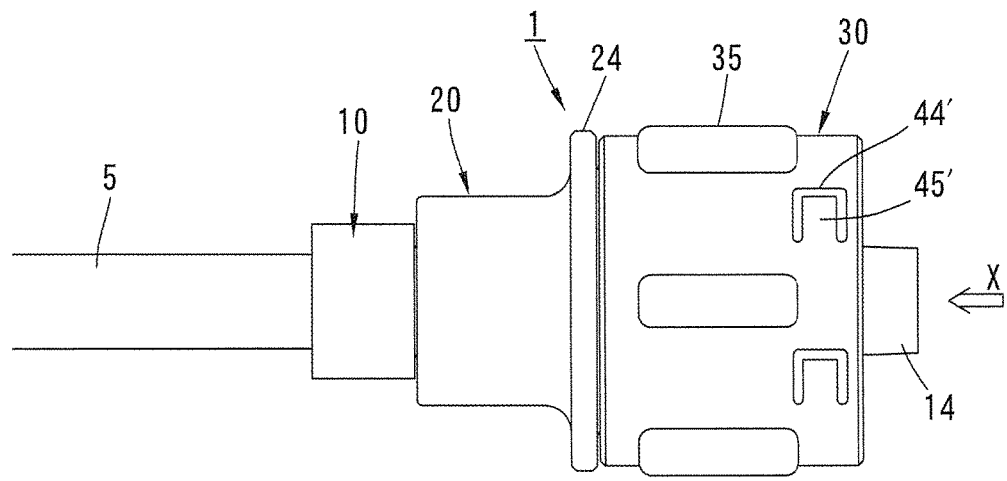
FIG. 11 is a side view of a male connector and an operating cylinder of a connecting structure for medical use according to a third embodiment of the present invention.
Figure 12:
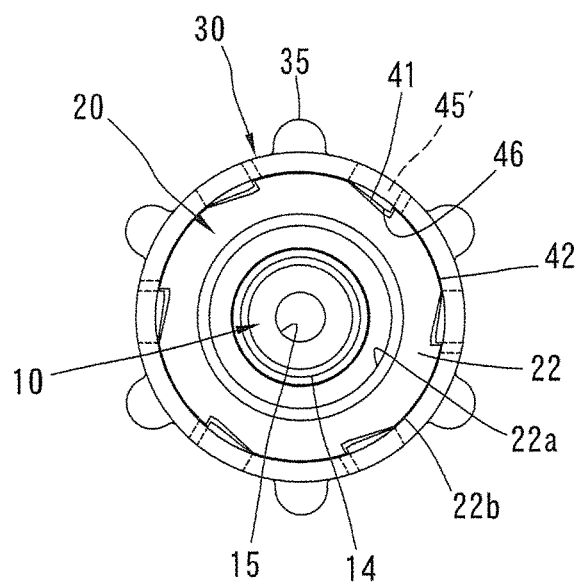
FIG. 12 is a front view, viewed from the direction of arrow X of FIG. 11.
Figure 13:
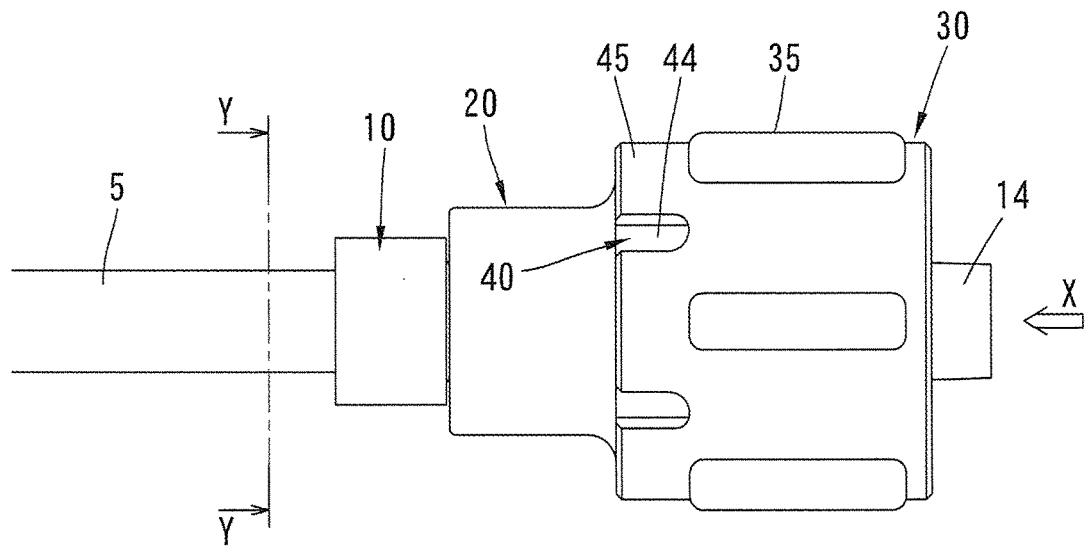
FIG. 13 is a side view of a male connector and an operating cylinder of a connecting structure for medical use according to a fourth embodiment of the present invention.
Figure 14:
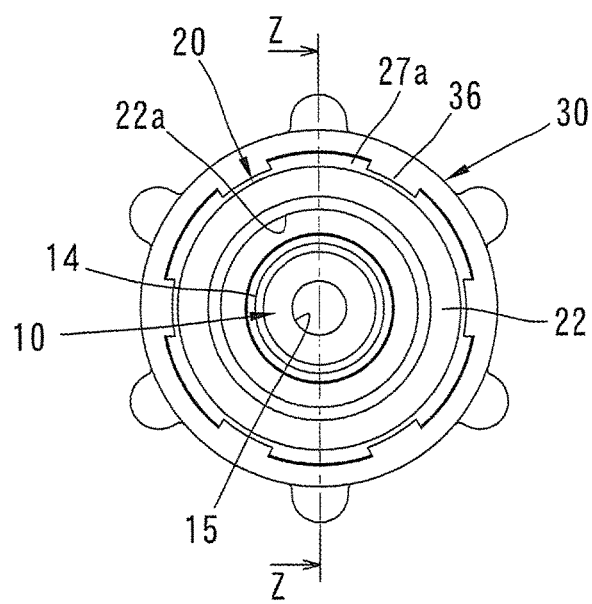
FIG. 14 is a front view, viewed from the direction of arrow X of FIG. 13.
Figure 15:
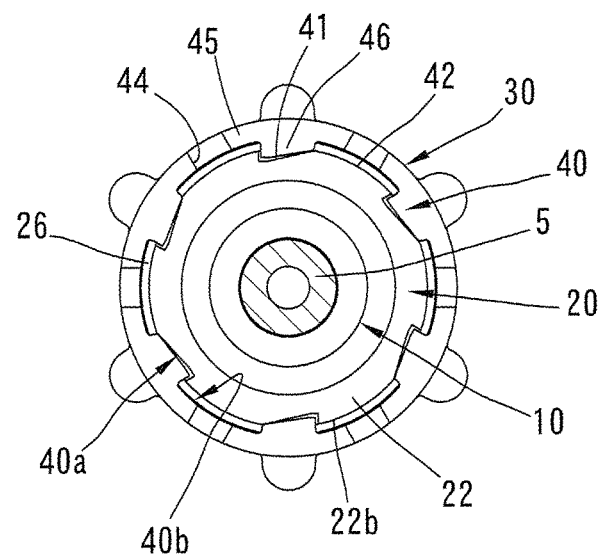
FIG. 15 is a cross-sectional view, taken along line Y-Y of FIG. 13.
Figure 16:
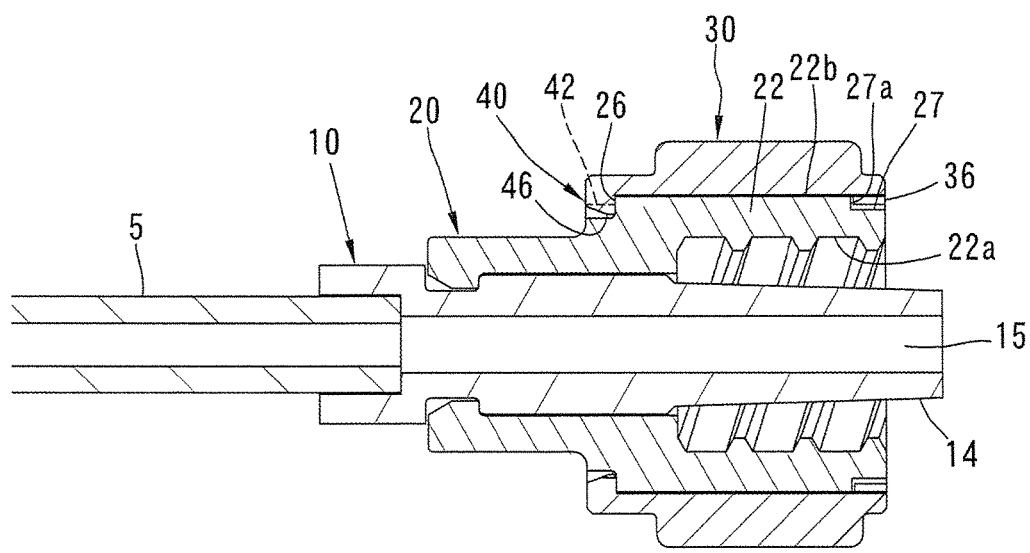
FIG. 16 is a cross-sectional view, taken along line Z-Z of FIG. 14.

In a third embodiment shown in FIGS. 11 and 12, slits 44' having a U-shaped configuration are formed in a distal end portion of an operating cylinder 30 evenly spaced apart in a circumferential direction. Areas surrounded by the slits 44' are provided as elastically deformable portions 45' that are elastically deformable in a radial direction. Engagement protrusions 46 similar to those of the first embodiment are formed in inner surfaces of the elastically deformable portions 45'. Engagement recesses 41 similar to those of the first embodiment are formed in an outer periphery of the support portion 22b of a threadedly engageable member 20.

In a fourth embodiment shown in FIGS. 13 to 16, a torque limiting mechanism 40 similar to that of the first embodiment is disposed on a basal end of an operating cylinder 30. Specifically, slits 44 are formed in a basal end portion of the operating cylinder 30 evenly spaced apart in a circumferential direction. The slits 44 extend in an axial direction from a basal end through a predetermined length. Areas between adjacent slits 44 are provided as elastically deformable portions 45. An engagement protrusion 46 is formed in an inner surface of each of the elastically deformable portions 45. Engagement recesses 41 similar to those of the first embodiment are formed in a basal end portion of a support portion 22b of a threadedly engageable member 20 evenly spaced apart in a circumferential direction.

An annular catch surface 26 extending orthogonal to a central axis is formed in the support portion 22b of the threadedly engageable member 20 at a portion adjacent to the engagement recess 41. The engagement protrusion 46 of the operating cylinder 30 is caught by the catch surface 26. An annular recess 27 is formed in a distal end portion of the support portion 22b. A deep end of the recess 27 serves as an annular catch surface 27a extending orthogonal to the central axis. A catch protrusion 36 protruding from an inner periphery of a distal end portion of the operating cylinder 30 is caught by the catch surface 27a. As a result, the operating cylinder 30 is immovable with respect to the threadedly engageable member 20 in the axial direction.

Figure 17:
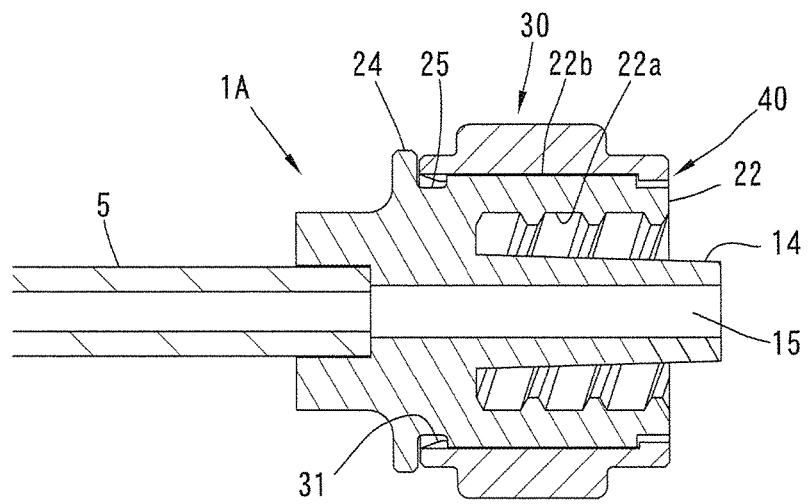
FIG. 17 is a cross-sectional view of a male connector and an operating cylinder of a connecting structure for medical use according to a fifth embodiment of the present invention.

In a male connector 1A (first connecting portion) of a fifth embodiment shown in FIG. 17, a circular cylindrical portion 22 having a female screw portion 22a and a support portion 22b is integrally formed with a male luer portion 14. Other features are same as those of the first embodiment.

Figure 18:
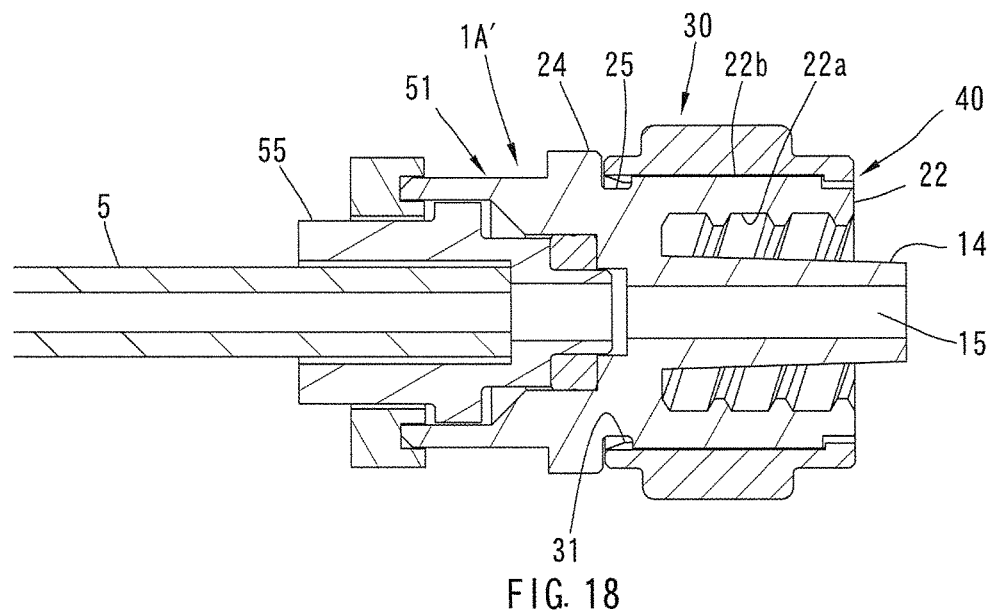
FIG. 18 is a cross-sectional view of a male connector and an operating cylinder of a connecting structure for medical use according to a sixth embodiment of the present invention.

A male connector 1A' of a sixth embodiment shown in FIG. 18 includes a body 51 having similar features to the male connector 1A of the fifth embodiment and an attachment 55 rotatably connected to the body 51. A tube 5 is fixed to the attachment 55.

Figure 19A:
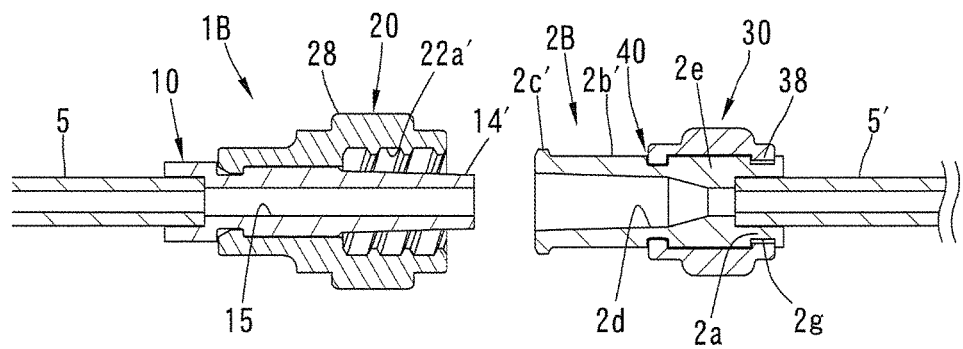
FIG. 19A is a cross-sectional view of a connecting structure for medical use according to a seventh embodiment of the present invention, showing a male connector and a female connector separate from each other.
Figure 19B:
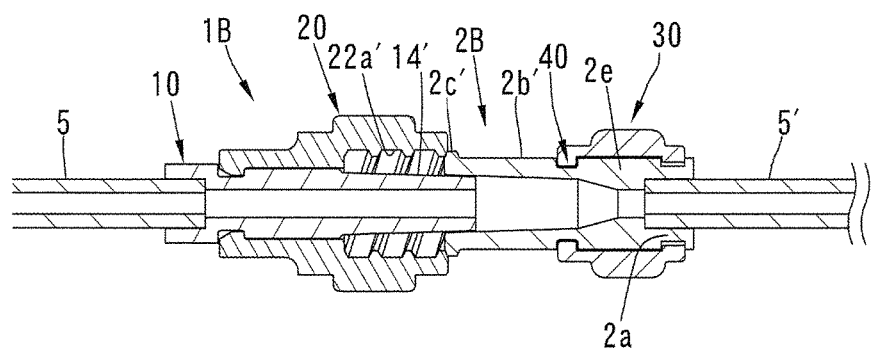
FIG. 19B is a cross-sectional view of the connecting structure for medical use according to the seventh embodiment of the present invention at a start of a connection work.
Figure 19C:
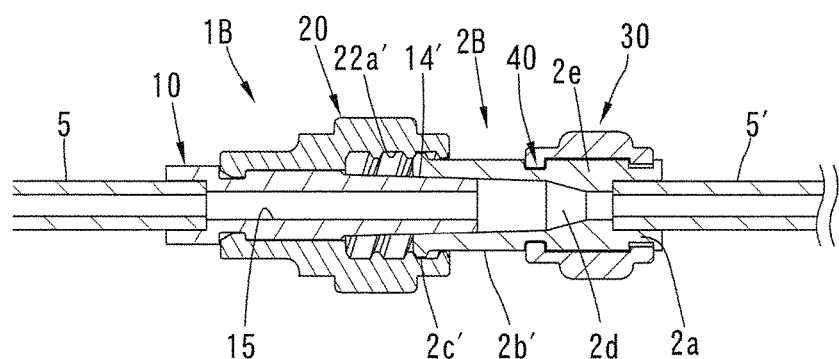
FIG. 19C is a cross-sectional view of the connecting structure for medical use according to the seventh embodiment of the present invention on completion of the connection work.
Figure 20:
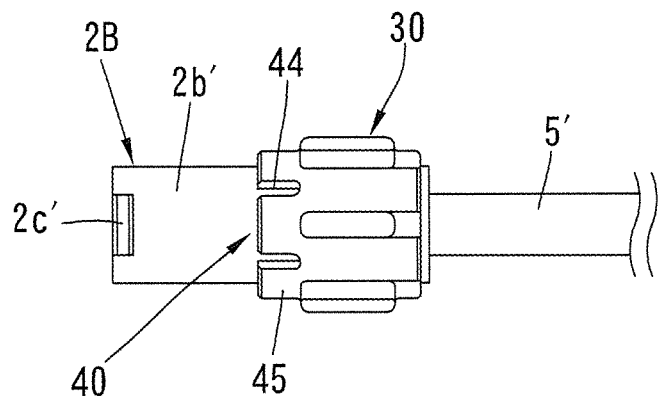
FIG. 20 is a side view of the female connector and an operating cylinder according to the seventh embodiment of the present invention.
Figure 21:
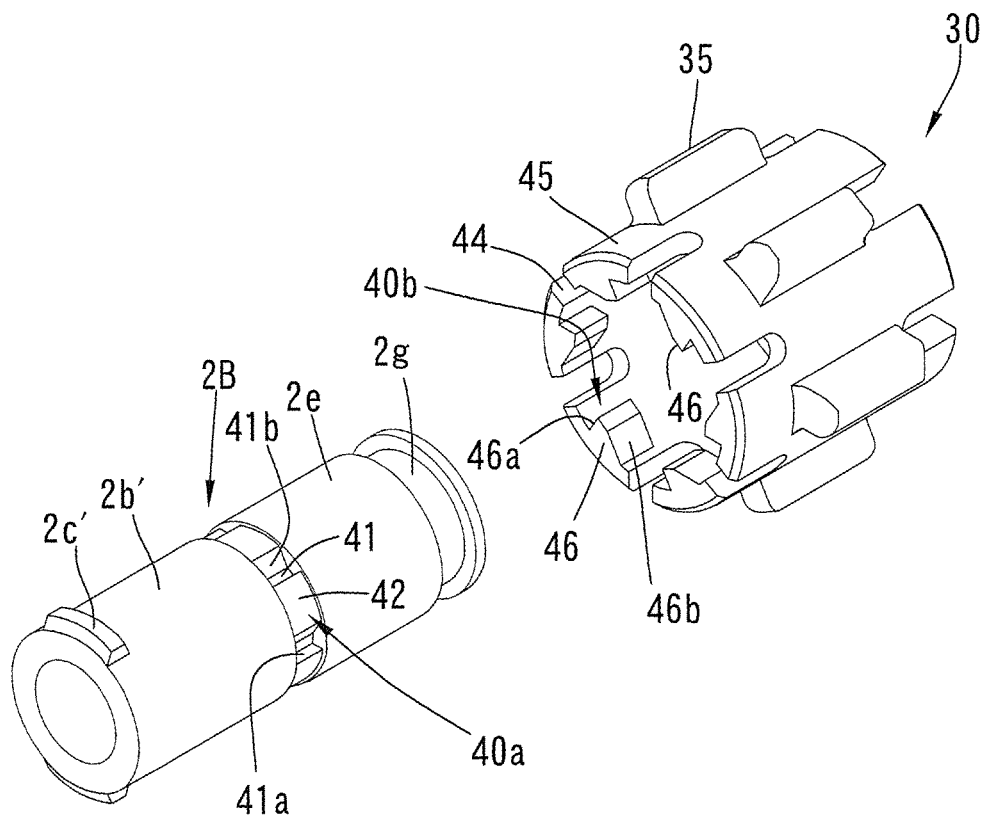
FIG. 21 is a perspective view of the seventh embodiment, showing the female connector and the operating cylinder separate from each other.

In a seventh embodiment shown in FIGS. 19 to 21, an operating cylinder 30 is attached to a female connector 2B. Accordingly, the female connector 2B is provided as a first connecting portion, a female luer portion 2b' is provided as a first sealing portion and protrusions 2c' are provided as a first threadedly engageable portion. A male connector 1B is provided as a second connecting portion, a male luer portion 14' is provided as a second sealing portion and a female screw portion 22a' is provided as a second threadedly engageable portion.

Features of the male connector 1B are similar to those of the male connector 1 of the first embodiment except that structures for attaching the operating cylinder 30 are not provided and a finger rest portion 28 is provided in an outer periphery of a threadedly engageable member 20.

An outer periphery of a basal end portion of the female connector 2B is provided as a support portion 2e. A torque limiting mechanism 40 is disposed between a distal end portion of the operating cylinder 30 and the support portion 2e of the female connector 2B. Specifically, engagement recesses 41 are formed in a first engaging area 40a of the support portion 2e of the female connector 2B evenly spaced apart in a circumferential direction in a similar fashion to the first embodiment. Slits 44, elastically deformable portions 45 and engagement protrusions 46 are formed in a second engaging area 40b of an inner periphery of a distal end portion of the operating cylinder 30 in a similar fashion to the first embodiment.

As shown in FIG. 19A, engagement protrusions 38 are formed in a basal end portion of the operating cylinder 30 such that the engagement protrusions 38 protrude inwardly in a radial direction and are evenly spaced apart in the circumferential direction. The engagement protrusions 38 are fitted in an annular engagement groove 2g formed in a basal end of the female connector 2B, and thereby the operating cylinder 30 is connected to the female connector 2B such that the operating cylinder 30 is rotatable but immovable in an axial direction.

In a state where a rotary torque is not applied to the operating cylinder 30, the engagement protrusions 46 are in the engagement recesses 41 of the female connector 2B.

As shown in FIG. 19A, the male connector 1B and the female connector 2B are coaxially brought closer to each other. Then, as shown in FIG. 19B, protrusions 2c' are abutted against an opening end of the female screw portion 22a' and the male luer portion 14' of the male connector 1B is inserted in a distal end portion of the female luer portion 2b' of the female connector 2B.

Next, the operating cylinder 30A is turned. This causes the threaded engagement between the protrusions 2c' and the female screw portion 22a' to be advanced. Thereby, a depth of insertion of the male luer portion 14' into the female luer portion 2b' is increased. When the male luer portion 14' and the female luer portion 2b' are joined together and a pressing force is increased, a torque required for turning the operating cylinder 30 is increased as a result of a frictional resistance working between the male luer portion 14' and the female luer portion 2b'. However, as mentioned above, the rotary torque can be controlled by the torque limiting mechanism 40.

Figure 22:
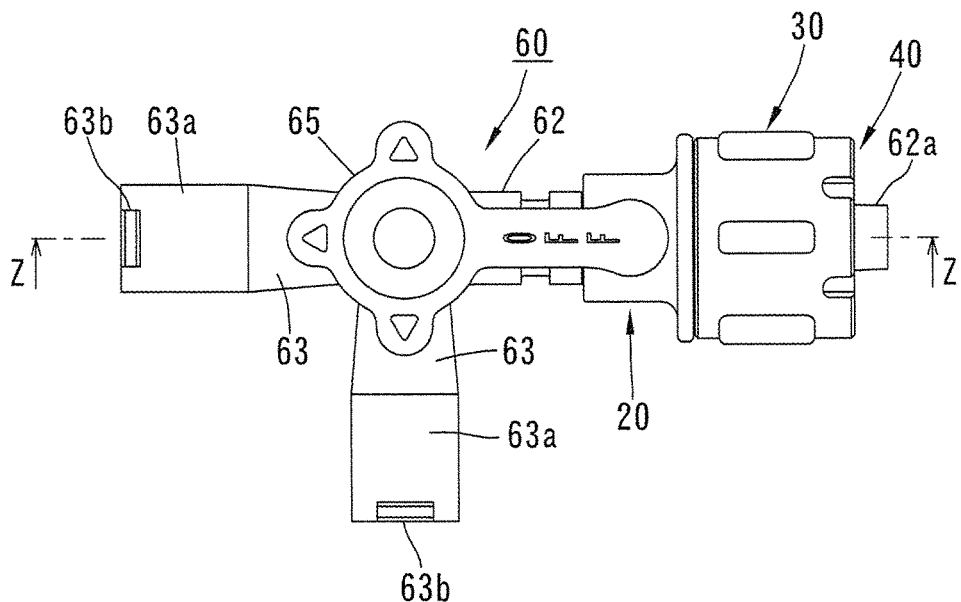
FIG. 22 is a plan view of a connecting structure for medical use according to an eighth embodiment, applied in a three-way stopcock.
Figure 23:
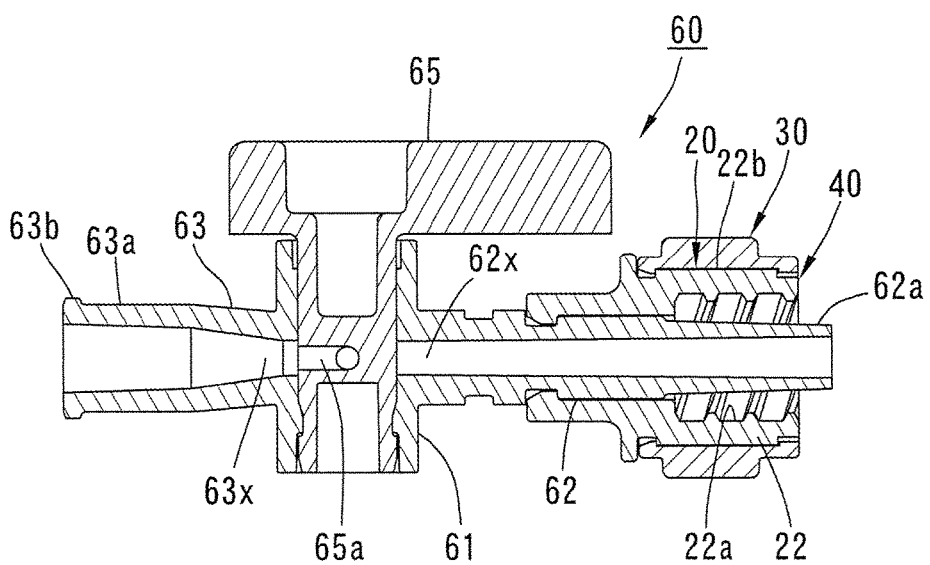
FIG. 23 is a cross-sectional view, taken along line Z-Z of FIG. 22.

In an eighth embodiment shown in FIGS. 22 and 23, the present invention is applied in a three-way stopcock 60 (stopper cock). The three-way stopcock 60 includes a body 61 having a cylindrical configuration and three flow pipe portions integrally formed in the body 61. One flow pipe portion 62 includes a male luer portion 62a (first sealing portion) in a distal end portion thereof and provides a first connecting portion in cooperation with a threadedly engageable member 20 that is similar to that of the first embodiment. As with the first embodiment, an operating cylinder 30 is disposed on the threadedly engageable member 20 and a torque limiting mechanism 40 is disposed between the threadedly engageable member 20 and the operating cylinder 30.

Female luer portions 63a, 63a and a protrusion 63b are formed in distal end portions of the other two flow pipe portions 63, 63.

A cock member 65 is received in the body 61. The cock member 65 includes a communication passage 65a having an L-shaped configuration. The cock member 65 selectively makes two of passages 62x, 63x, 63x of the flow pipe portions 62, 63, 63 communicate with each other by turning operation.

A female connector 2 that may be fixed to a tube 5' shown in FIG. 1A for example, is connected to the flow pipe portion 62. During the connecting work, the operating cylinder 30 and the torque limiting mechanism 40 work in a similar manner to the first embodiment, and therefore explanation thereof is omitted.

Alternatively, the flow pipe portion 63 may be provided as a second connecting portion and a male connector 1 similar to that of the first embodiment may be connected to the flow pipe portion 63.

Figure 24:
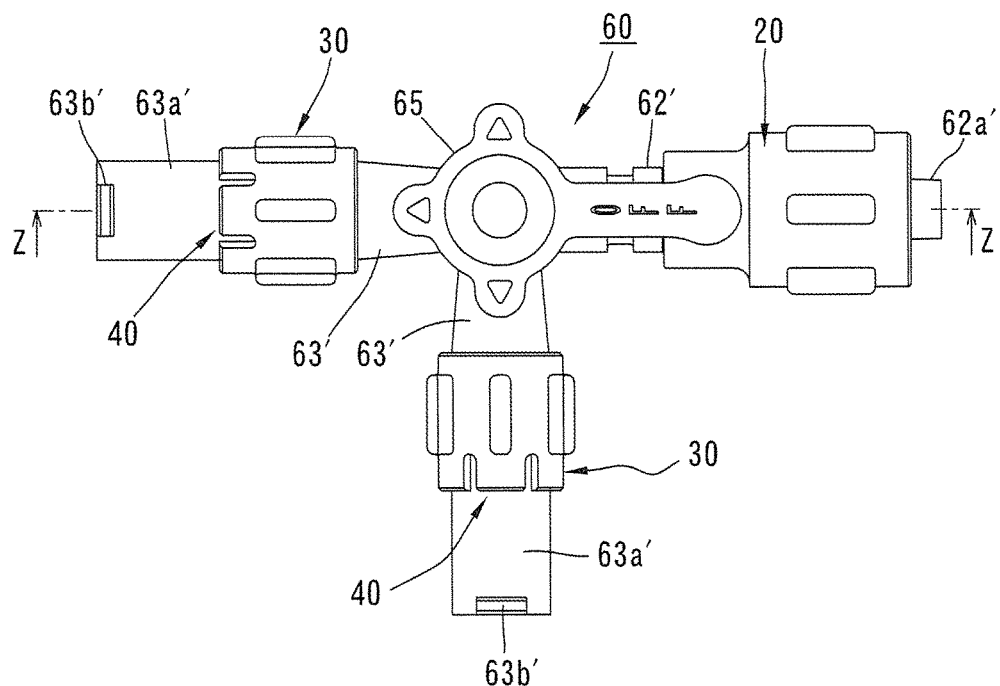
FIG. 24 is a plan view of a connecting structure for medical use according to a ninth embodiment of the present invention, applied in a three-way stopcock.
Figure 25:
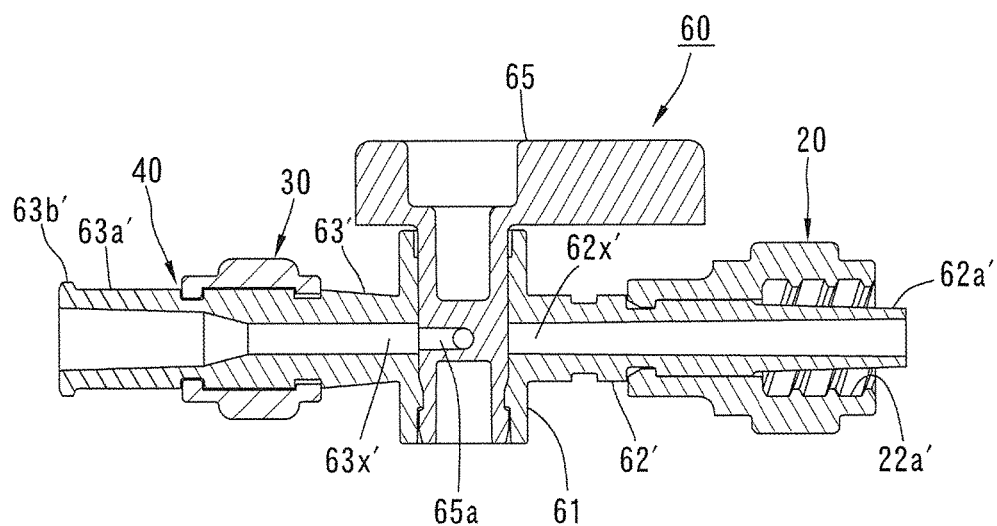
FIG. 25 is a cross-sectional view, taken along line Z-Z of FIG. 24.

In a ninth embodiment shown in FIGS. 24 and 25, the present invention is applied in a three-way stopcock 60 as with the eighth embodiment. A flow pipe portion 63' of the three-way stopcock 60 is provided as a first connecting portion, a female luer portion 63a' of the flow pipe portion 63' is provided as a first sealing portion and a protrusion 63b' is provided as a first threadedly engageable portion. A portion of the flow pipe portion 63' closer to a basal end thereof than the female luer portion 63a' is provided as a support portion that supports an operating cylinder 30.

A male connector 1B fixed to a tube 5 shown in FIG. 19A, for example, may be connected to the flow pipe portion 63'. During the connecting work, the operating cylinder 30 and a torque limiting mechanism 40 work in a similar manner to the seventh embodiment, and therefore explanation thereof is omitted.

When a flow pipe portion 62' and a threadedly engageable member 20 in cooperation with each other are provided as a second connecting portion having a similar features to a male connector 1B shown in FIG. 19A, a female connector 2B shown in FIG. 19A is connected to the flow pipe portion 62'

Figure 26:
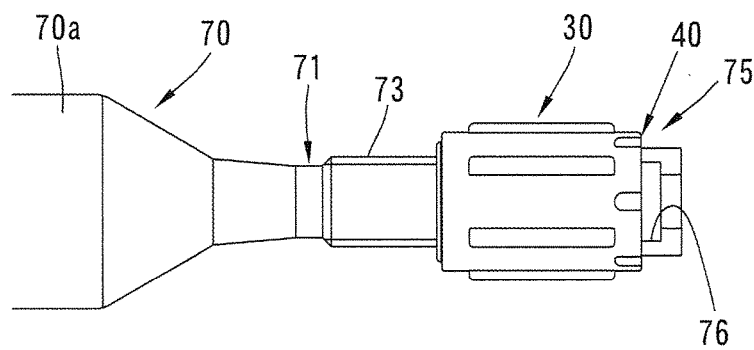
FIG. 26 is a plan view of a connecting structure for medical use according to a tenth embodiment of the present invention, applied in a syringe.
Figure 27:
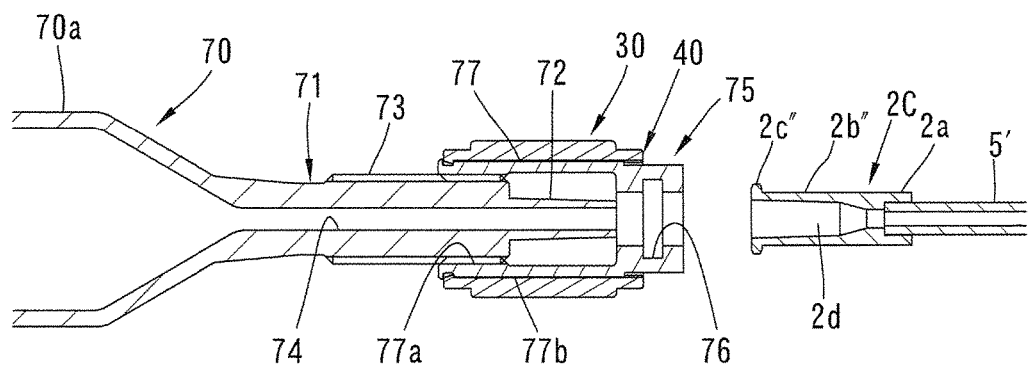
FIG. 27 is a cross-sectional view of the connecting structure for medical use applied in a syringe, showing the structure in a separate state.
Figure 28:
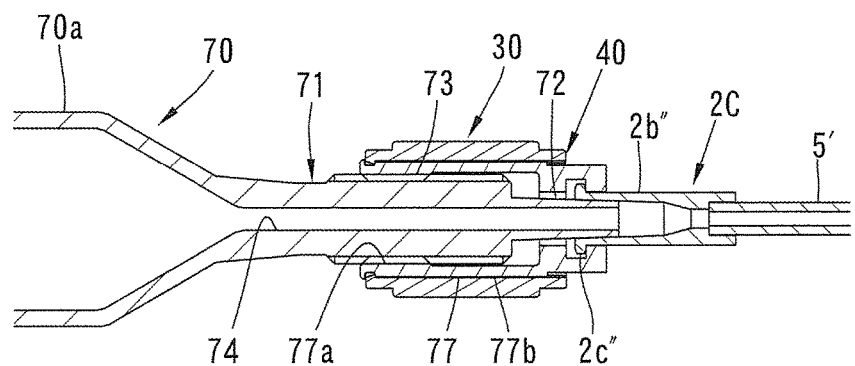
FIG. 28 is a cross-sectional view, showing the syringe connected with a tube.

In a tenth embodiment shown in FIGS. 26 to 28, the present invention is applied in a contrast medium syringe 70. The syringe 70 includes a liquid outlet portion 71. The liquid outlet portion 71 is provided as a second connecting portion. The liquid outlet portion 71 includes a male luer portion 72 (second sealing portion) in a distal end portion thereof. The liquid outlet portion 71 includes a male screw portion 73 (second threadedly engageable portion) in an outer periphery thereof at a portion closer to a barrel portion 70a of the syringe 70 than the male luer portion 72. The liquid outlet portion 71 includes a passage 74 that extends along a central axis thereof and continues to an inner space of the barrel portion 70a.

A female luer member 2C fixed to an end of a tube 5', for example, may be connected to the male luer portion 72 of the syringe 70 via an attachment 75 having a cylindrical configuration. The female luer member 2C and the attachment 75 constitute a first connecting portion.

The attachment 75 includes a receiving recess 76 in a basal end portion thereof. The receiving recess 76 can receive protrusions 2c" at a distal end portion of the female luer member 2C such that the protrusions 2c" are removable in a radial direction.

The attachment 75 includes a circular cylindrical portion 77. A female screw portion 77a (first threadedly engageable portion) is formed in an inner periphery of the circular cylindrical portion 77. An outer periphery of the circular cylindrical portion 77 is provided as a support portion 77b. An operating cylinder 30 is attached to the support portion 77b such that the operating cylinder 30 is rotatable but immovable in an axial direction. Structures for attaching the operating cylinder 30 and a torque limiting mechanism 40 are similar to those of the first embodiment, and therefore detailed description thereof is omitted.

In a condition where the female luer member 2C is removably connected to the attachment 75, the male luer portion 72 and a female luer portion 2b" (first sealing portion) can be joined together by applying a rotary torque to the operating cylinder 30 to advance the threaded engagement between the female screw portion 77a of the attachment 75 and the male screw portion 73 of the liquid outlet portion 71. Torque can be controlled by the torque limiting mechanism 40 during the connecting work in a similar manner to all the foregoing embodiments.

Alternatively, a threadedly engageable member 20, the operating cylinder 30 and the torque limiting mechanism 40 may be mounted on the liquid outlet portion 71 of the syringe 70 in a similar manner to the first embodiment and the female connector 2 of the first embodiment may be connected to the liquid outlet portion 71.

Figure 29:
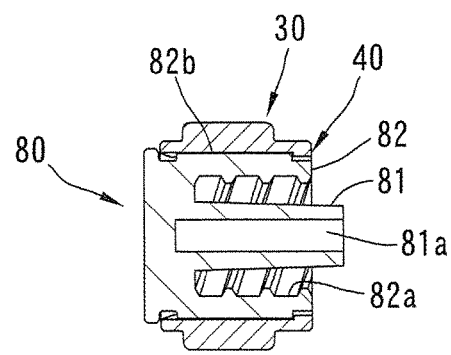
FIG. 29 is a cross-sectional view of a male closing member and an operating cylinder of a connecting structure for medical use according to an eleventh embodiment of the present invention.
Figure 30:
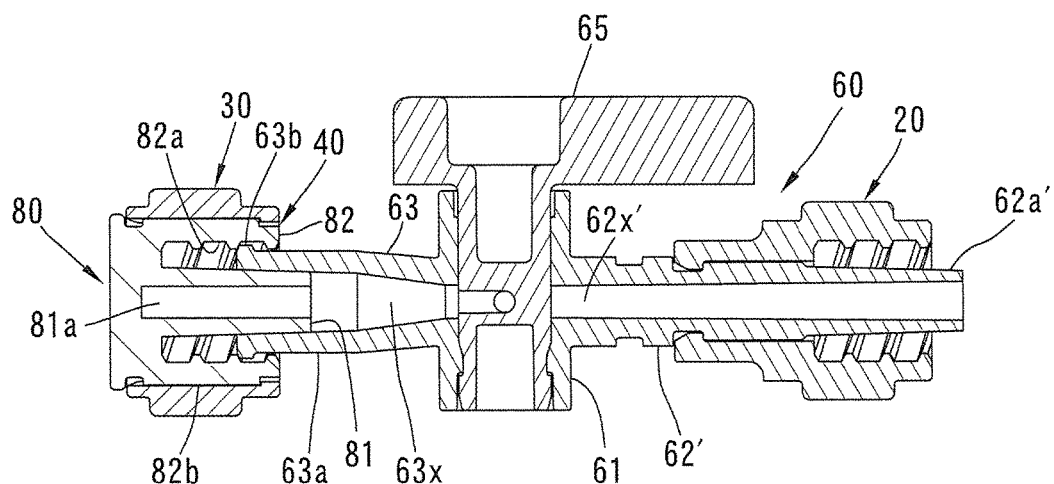
FIG. 30 is a cross-sectional view, showing the male closing member connected to a female luer portion of a three-way stopcock.

In an eleventh embodiment shown in FIGS. 29 and 30, the present invention is applied in a passage blocking structure. A male blocking member 80 (first connecting portion) integrally includes a male luer portion 81 (first sealing portion) and a circular cylindrical portion 82. A passage 81a of the male luer portion 81 is blocked at a basal end. The circular cylindrical portion 82 includes a female screw portion 82a (first threadedly engageable portion) in an inner periphery thereof. An outer periphery of the circular cylindrical portion 82 is provided as a support portion 82b for attaching an operating cylinder 30 thereon. Structures for attaching the operating cylinder 30 and a torque limiting mechanism 40 are similar to those of the first embodiment, and therefore detailed description thereof is omitted.

The male blocking member 80 is connected to a female luer portion, which may be a flow pipe portion 63 (second connecting portion) of a three-way stopcock 60, for example. The operating cylinder 30 is turned to advance the threaded engagement between the female screw portion 82a of the male blocking member 80 and a protrusion 63b (second threadedly engageable portion), thereby joining the male luer portion 81 and a female luer portion 63a (second sealing portion) together. As a result, a passage 63x of the flow pipe portion 63 can be blocked.

Figure 31:
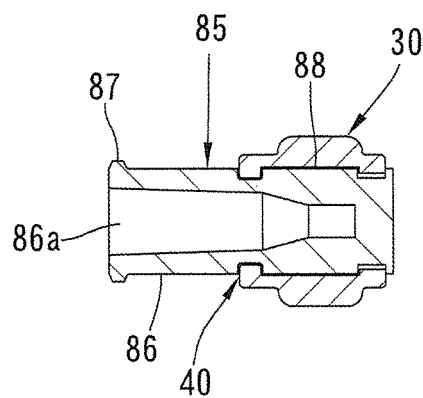
FIG. 31 is a cross-sectional view of a female closing member and an operating cylinder of a connecting structure for medical use according to a twelfth embodiment of the present invention.
Figure 32:
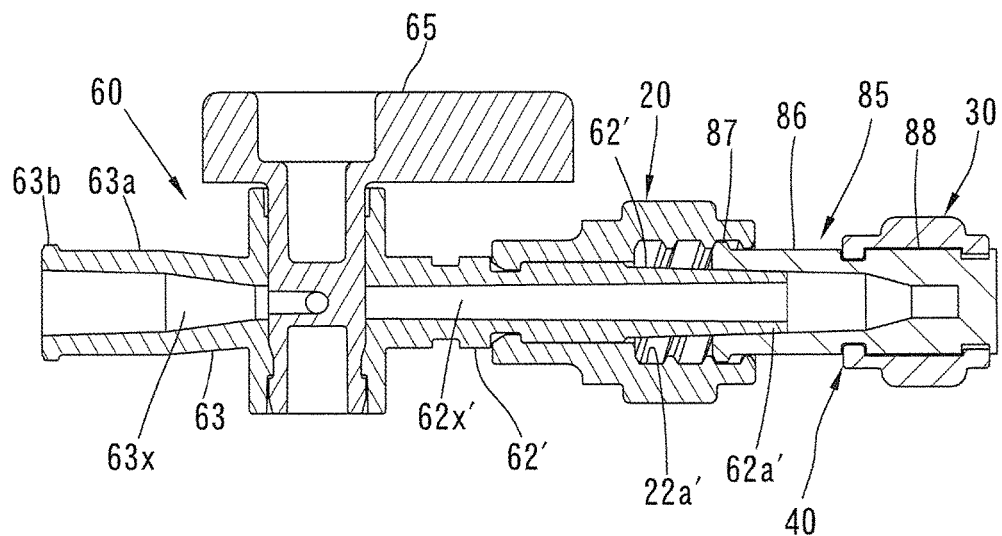
FIG. 32 is a cross-sectional view, showing the female closing member connected to a male luer portion of a three-way stopcock.

The present invention is applied in a passage blocking structure in a twelfth embodiment shown in FIGS. 31 and 32 as well.

A female blocking member 85 (first connecting portion) includes a female luer portion 86 (first sealing portion) on a distal end thereof. A protrusion 87 (first threadedly engageable portion) is formed in an outer periphery of a distal end of the female lure portion 86. The female blocking member 85 further includes a support portion 88 for attaching an operating cylinder 30 thereon on a basal end thereof. Structures for attaching the operating cylinder 30 and a torque limiting mechanism 40 are similar to those of the seventh embodiment (see FIG. 19), and therefore detailed description thereof is omitted. A passage 86a of the female luer portion 86 is blocked on a basal end thereof.

The female blocking member 85 may be connected to a flow pipe portion 62' (second connecting portion) of a three-way stopcock 60, for example. The operating cylinder 30 is turned to advance the threaded engagement between the protrusion 87 of the female blocking member 85 and a female screw portion 22a' (second threadedly engageable portion) of a threadedly engageable member 20 disposed on the flow pipe portion 62', thereby joining a male luer portion 62a' (second sealing portion) of the flow pipe portion 62' and the female luer portion 86 together. As a result, a passage 62x' of the flow pipe portion 62' can be blocked.

In the first embodiment shown in FIGS. 1 to 6, a female blocking member may be made by blocking a basal end of the passage 2d of the connector 2.

In the seventh embodiment shown in FIGS. 19 to 21, a male blocking member may be made by blocking a basal end of the passage 15 of the connector 1B.

The present invention is not limited to the embodiment described above. Various modifications can be made without departing from the scope and spirit of this invention. Features of many of the embodiments mentioned above may be combined with other features of other embodiments.

The present invention may be applied in connecting structures for medical use other than a tube, a stopcock and a syringe.

In the embodiments described above, the first connecting portion and the operating cylinder respectively have a plurality of the first engageable portions and the second engageable portions. Alternatively, the first connecting portion and the operating cylinder may respectively have one first engageable portion and one second engageable portion.

The rotation of the operating cylinder with respect to the threadedly engageable portion of the second connecting portion is relative. Therefore, the threadedly engageable portion of the second connecting portion may be rotated with the operating cylinder not being moved.

INDUSTRIAL APPLICABILITY

The present invention may be applied in connecting structures for connecting medical components such as a tube, a stopcock and a syringe.

The invention claimed is:

1. A connecting structure for medical use comprising:
a first connecting portion; and
a second connecting portion wherein:
the first connecting portion comprises a first threadedly engageable portion and the second connecting portion comprises a second threadedly engageable portion, the first threadedly engageable portion and the second threadedly engageable portion being threadedly engageable with each other;
the first connecting portion comprises a first sealing portion and the second connecting portion comprises a second sealing portion, the first sealing portion and the second sealing portion being joinable to each other by advancement of a threaded engagement between the first threadedly engageable portion and the second threadedly engageable portion;
one of the first and second sealing portions is a male luer portion having a tapered outer periphery and the other of the first and second sealing portions is a female luer portion having a tapered inner periphery; and
the male luer portion and the female luer portion can be sealed together by joining the outer periphery of the male luer portion and the inner periphery of the female luer portion, wherein:
the first connecting portion comprises a support portion that is integral with the first threadedly engageable portion;
an operating cylinder is mounted on an outer periphery of the support portion such that the operating cylinder is not movable in an axial direction;
a torque limiting mechanism is disposed between the support portion of the first connecting portion and the operating cylinder; and
the torque limiting mechanism is constructed and arranged such that:
(a) when the operating cylinder is turned in a threaded engagement loosening direction with respect to the second connecting portion, the support portion of the first connecting portion is turned together with the operating cylinder;
(b) in a process in which the operating cylinder is turned in a threaded engagement advancing direction with respect to the second connecting portion, the support portion of the first connecting portion is turned together with the operating cylinder until a rotary torque applied to the operating cylinder reaches a predetermined torque; and
(c) in the process in which the operating cylinder is turned in the threaded engagement advancing direction with respect to the second connecting portion, the operating cylinder is turned free from the support portion of the first connecting portion when the rotary torque applied to the operating cylinder reaches the predetermined torque as a result of a resistance generated by joining of the first sealing portion and the second sealing portion;

the support portion comprises an annular first engaging area in the outer periphery thereof and the operating cylinder comprises an annular second engaging area in an inner periphery thereof, the first engaging area and the second engaging area opposed to each other in a radial direction;

an inner periphery of one end portion of the operating cylinder in the axial direction is provided as the second engaging area;

the operating cylinder has a plurality of slits extending in the axial direction thereof formed in the one end portion thereof, the plurality of slits being evenly spaced apart in a circumferential direction;

areas between the slits are provided as elastically deformable portions which are elastically deformable in a radial direction independently from each other;

the torque limiting mechanism comprises a plurality of first engageable portions formed in the first engaging area evenly spaced apart in the circumferential direction and second engageable portions formed in inner surfaces of the elastically deformable portions;

one side of the second engageable portion comprises a steep catch surface and one side of the first engageable portion comprises a steep catch surface;

at least one of an other side of the second engageable portion and an other side of the first engageable portion comprises an inclined surface;

when the operating cylinder is turned in the threaded engagement loosening direction with respect to the second connecting portion, the one side of the second engageable portion is caught by the one side of the first engageable portion opposed to the one side of the second engageable portion in the circumferential direction, thereby the support portion of the first connecting portion being turned together with the operating cylinder;

in the process in which the operating cylinder is turned in the threaded engagement advancing direction with respect to the second connecting portion, the other side of the second engageable portion is caught by the other side of the first engageable portion, thereby the support portion of the first connecting portion being turned together with the operating cylinder until the rotary torque applied to the operating cylinder reaches the predetermined torque; and in the process in which the operating cylinder is turned in the threaded engagement advancing direction with respect to the second connecting portion, the second engageable portion is moved beyond the first engageable portion accompanied by radially outwardly elastic deformation of the elastically deformable portions when the rotary torque applied to the operating cylinder reaches the predetermined torque as a result of the resistance generated by the joining of the first sealing portion and the second sealing portion, thereby the operating cylinder being turned free.

2. The connecting structure for medical use according to claim 1, wherein:
engagement recesses as the first engageable portions are formed in the first engaging area of the support portion;
engagement protrusions as the second engageable portions are formed in the second engaging area of the operating cylinder; and
in a condition where the rotary torque is not applied to the operating cylinder, the engagement protrusions are received in the engagement recesses.

3. The connecting structure for medical use according to claim 1, wherein:
the first connecting portion is disposed in a first medical component that comprises a passage;
the second connecting portion is disposed in a second medical component that comprises a passage; and
the passage of the first medical component and the passage of the second medical component are brought to communicate with each other by connection of the first connecting portion and the second connecting portion.

4. The connecting structure for medical use according to claim 1, wherein the second engageable portions are formed in the inner surfaces of distal end portions of the elastically deformable portions, and a dimension of the second engageable portions in an axial direction is smaller than the length of the slits.

* * * * *